United States Patent [19]
Daluge et al.

[11] Patent Number: 5,776,940
[45] Date of Patent: Jul. 7, 1998

[54] PHENYLXANTHINE DERIVATIVES

[75] Inventors: Susan Mary Daluge; Helen Lyng White, both of Chapel Hill, N.C.

[73] Assignee: Glaxo Wellcome Inc., Research Triangle Park, N.C.

[21] Appl. No.: 776,454

[22] PCT Filed: Jul. 31, 1995

[86] PCT No.: PCT/GB95/01808

§ 371 Date: Jan. 24, 1997

§ 102(e) Date: Jan. 24, 1997

[87] PCT Pub. No.: WO96/04280

PCT Pub. Date: Feb. 15, 1996

[30] Foreign Application Priority Data

Aug. 1, 1994 [GB] United Kingdom ............. 9415529

[51] Int. Cl.$^6$ .................. A61K 31/52; C07D 473/06; C07D 239/54; C07D 239/56
[52] U.S. Cl. .................. 514/263; 544/271; 544/311
[58] Field of Search ............. 544/271; 514/263

[56] References Cited

U.S. PATENT DOCUMENTS

| | | | |
|---|---|---|---|
| 4,980,379 | 12/1990 | Belardinelli ............. | 514/821 |
| 5,015,647 | 5/1991 | Daluge et al. ............ | 514/263 |
| 5,300,298 | 4/1994 | La Noue ................ | 514/261 |

FOREIGN PATENT DOCUMENTS

| | | |
|---|---|---|
| 0 203 721 | 12/1986 | European Pat. Off. . |
| 243192 | 10/1987 | European Pat. Off. . |
| 0 590 919 | 4/1994 | European Pat. Off. . |
| 2 135 311 | 8/1984 | United Kingdom . |

*Primary Examiner*—Mark L. Berch
*Attorney, Agent, or Firm*—LaVonda R. DeWitt

[57] ABSTRACT

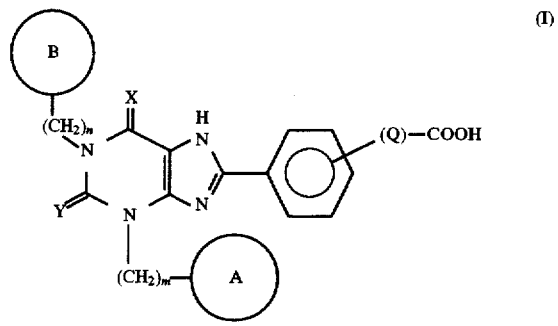

The present invention relates to novel compounds of formula (I), processes for their preparation, pharmaceutical formulations containing them, and their use in medicine, particularly in the prophylaxis and treatment of septic shock, allergic, and inflammatory conditions, as well as neurodegeneration.

6 Claims, No Drawings

PHENYLXANTHINE DERIVATIVES

This application is filed pursuant to 35 U.S.C. § 371 as a United States National Phase Application of International Application No. PCT/GB95/01808 filed Jul. 31, 1995 which claims priority from GB9415529.8 filed Aug. 1, 1994.

The present invention relates to novel phenyl xanthine derivatives, processes for their preparation, pharmaceutical formulations comprising them, and their use in medicine, particularly in the prophylaxis and treatment of septic shock, allergic, and inflammatory conditions, as well as neurodegeneration.

Septic shock is induced by means of a complex series of events involving many different pathways and mediators of disease response (see for instance, The Lancet, Vol. 338 (1991), p732–739, and annals of internal medicine Vol. 115 (1991), p457–469), including, inter alia, products of arachidonic acid metabolism and platelet aggregation. These mediators are also involved in inflammatory conditions and are now implicated in the neurodegeneration and dementia associated with HIV infection.

The enzymes arachidonate 5-lipoxygenase, arachidonate cyclooxygenase, and lyso-PAF: acetyl -CoA acetyltransferase are all implicated in the mediation of allergic and inflammatory conditions. Inhibitors of each of these enzymes have previously been disclosed, however, there exists a continuing need for further therapies for the treatment of diseases which involve these pathways. Furthermore, some of the compounds of the present invention have been found to inhibit all three of these enzymes and could thus offer the possibility of a synergistic treatment of allergic and inflammatory conditions.

EP-B-0-203-721 describes phenyl xanthine compounds which exhibit activity as adenosine antagonists and are of formula wherein inter alia:

$X_1$ and $X_2$ are independently selected from hydrogen, $C_{1-4}$ alkyl $C_{2-6}$ alkenyl and $C_{7-12}$ aralkyl;

one of $X_3$ and $X_4$ is hydrogen and the other is a group —Y—Z wherein Y is $C_{2-6}$ alkenylene and Z is carboxy;

$X_5$ and $X_6$ are independently oxygen or sulphur.

WO 94/03456 discloses further adenosine antagonists of formula wherein inter alia $R_1$ is hydrogen, $C_{1-6}$ alkyl, $C_{3-6}$ alkenyl, or $C_{3-6}$ alkynyl;

$R_2$ is different to $R_1$ and is selected from hydrogen, $C_{1-8}$ alkyl, and $C_{3-7}$ cycloalkyl-$C_{1-6}$ alkyl;

$R_3$ is phenyl optionally substituted by —COOH; and $R_4$ is hydrogen.

According to the present invention, there is provided a compound of formula (I):

Wherein m and n are independently integers from 0 to 10;

X and Y are independently oxygen or sulphur;

(—Q—) is (—$CH_2$—)$_p$ or (—CH=CH—)$_p$ where p is an integer of from 1 to 4; and A and B are independently methyl, branched $C_{3-6}$ alkyl, $C_{3-8}$ cycloalkyl or $C_{3-8}$ cycloalkenyl;

with the proviso that at least one of A and B is either $C_{3-8}$ cycloalkyl or $C_{3-8}$ cycloalkenyl;

or a salt, solvate, or pharmaceutically acceptable ester or amide, thereof.

Preferably, X and Y are both oxygen.

Preferably, m and n are independently integers from 0 to 4, more preferably, from 0 to 2.

Preferably Q is —$CH_2CH_2$— or —CH=CH—, most preferably —CH=CH—.

Preferably the invention provides a compound wherein;

m and n are both 1;

(Q) is attached at the 4 position and is —CH=CH—; and

X and Y are both oxygen.

or a salt, solvate, or pharmaceutically acceptable ester or amide thereof

Most preferably the invention provides a compound wherein A and B are both $C_{3-8}$ cycloalkyl, particularly cyclohexyl.

The compounds of the present invention are capable of existing as geometric and optical isomers. All such isomers, individually and as mixtures, are included within the scope of the present invention. Compounds in the form of the E-geometric isomers are preferred.

Particularly prefered compounds of the invention include (E)-4-(1, 3-Bis(cyclohexylmethyl)-1, 2, 3, 6-tetrahydro-2, 6-dioxo-9H-purin-8-yl)cinnamic acid; and (E)-4-{1,3 Bis[2-(1-cyclohexen-1-yl)ethyl]-1,2,3,6-tetrahydro-2,6-dioxo-9H-purin-8-yl}cinnamic acid;

or a salt, solvate, or pharmaceutically acceptable ester or amide thereof

Physiologically acceptable salts are particularly suitable for medical applications because of their greater aqueous solubility relative to the parent, ie acidic, compounds. Such salts must clearly have a physiologically acceptable cation. Suitable physiologically acceptable salts of the compounds of the present invention include ammonium salts, alkali metal salts such as sodium and potassium salts, alkaline earth salts such as magnesium and calcium salts and salts formed from organic bases, for example amino salts derived from mono-, di, or tri- (lower alkyl) amines; basic amino acids such as lysine, or (lower alkanol) amines such as triethanolamine and salts with heterocyclic amines such as piperidine, pyridine, piperazine and morpholine. The sodium and ammonium salts are particularly preferred for medical purposes. Salts having a non-physiologically acceptable cation are within the scope of the invention as useful intermediates for the preparation of physiologically acceptable salts and/or for use in non-therapeutic, for example, in vitro, situations.

As mentioned hereinbefore, compounds of formula (I) and salts, solvates, and pharmaceutically acceptable esters or amides thereof have use in the prophylaxis and treatment of clinical conditions for which an inhibitor of one or more of arachidonate 5-lipoxygenase, arachidonate cyclooxygenase, and lyso-PAF: acetyl -CoA acetyltransferase is indicated, as demonstrated hereinafter in the 5-lipoxygenase, cyclooxygenase, and lyso-PAF: acetyl -CoA acetyltransferase inhibition assays in which representative compounds of the present invention have been shown to be active. For example, the ability of compounds of formula (I) to inhibit arachidonate 5-lipoxygenase, arachidonate cyclooxygenase, and lyso-PAF: acetyl -CoA acetyltransferase, renders them useful for the prophylaxis and treatment of spasmogenic conditions, allergic conditions, conditions involving blood platelet aggregation, and inflammatory conditions.

Examples of spasmogenic conditions are those involving smooth muscle tissue, especially airway smooth muscle constriction such as asthma (including idiopathic bronchial asthma), bronchitis and arterial smooth muscle constriction such as coronary spasm (including that associated with myocardial infarction, which may or may not lead to left ventricular failure resulting in cardiac asthma), ischemia-induced myocardial injury, and cerebral spasm or 'stroke' (which may lead to central nervous pathophysiology). Other examples include bowel disease caused by abnormal colonic muscular contraction such as the conditions known as inflammatory bowel disorder, 'spastic colon' and 'mucous colitis'.

Examples of allergic conditions are extrinsic asthma, allergic skin diseases having a total or partial allergic origin, such as eczema, allergic bowel diseases (including coeliac disease), allergic eye conditions, such as hayfever (which may additionally or alternatively affect the upper respiratory tract), allergic rhinitis, and allergic conjunctivitis.

Examples of conditions involving blood platelet aggregation are those resulting from thrombosis, including 'strokes' having a total or partial thrombotic origin, coronary thrombosis, phlebitis and phlebothrombosis (the latter two conditions also possibly being associated with inflammation).

Examples of ivory conditions are those of the lungs, joints, eyes, bowel, skin, and heart; particularly those associated with the infiltration of leucocytes into inflamed tissue. Inflammatory lung conditions include asthma, adult respiratory distress syndrome, bronchitis and cystic fibrosis (which may additionally or alternatively involve the bowel or other tissue(s)). Inflammatory joint conditions include rheumatoid arthritis, rheumatoid spondylitis, osteoarthritis, gouty arthritis and other arthritic conditions. Inflammatory eye conditions include uveitis (including iritis) and conjunctivitis. Inflammatory bowel conditions include Crohn's disease, ulcerative colitis and distal proctitis. Inflammatory skin diseases include those associated with cell proliferation, such as psoriasis, eczema and dermatitis (whether or not of allergic origin). Inflammatory conditions of the heart include coronary infarct damage. Other inflammatory conditions include tissue necrosis in chronic inflammation, endotoxin shock, smooth muscle proliferation disorders (for example, restenosis following angioplasty), and tissue rejection following transplant surgery.

Accordingly, the present invention provides a method for the prophylaxis or treatment of a clinical condition in a mammal, such as a human, for which an inhibitor of one or more of arachidonate 5-lipoxygenase, arachidonate cyclooxygenase, and lyso-PAF: acetyl -CoA acetyltransferase is indicated, for example, a spasmogenic condition, an allergic condition, a condition involving blood platelet aggregation, or an inflammatory condition; which comprises administration of a therapeutically effective amount of a compound of formula (I), or a pharmaceutically acceptable salt, solvate, ester, or amide thereof. The present invention ether provides a method for the prophylaxis or treatment of septic shock in a mammal, such as a human, which comprises administration of a therapeutically effective amount of a compound of formula (I), or a pharmaceutically acceptable salt, solvate, ester, or amide thereof. The present invention still further provides a method for the prophylaxis or treatment of neurodegeneration or dementia associated with HIV infection in a mammal, such as a human, which comprises administration of a therapeutically effective amount of a compound of formula (I), or a pharmaceutically acceptable salt, solvate, ester, or amide thereof.

In the alternative, there is also provided a compound of formula (I), or a pharmaceutically acceptable salt, solvate, ester, or amide thereof for use in medical therapy, particularly, for use in the prophylaxis or treatment of a clinical condition in a mammal, such as a human, for which an inhibitor of one or more of arachidonate 5-lipoxygenase, arachidonate cyclooxygenase, and lyso-PAF: acetyl -CoA acetyltransferase is indicated; for example a spasmogenic condition, an allergic condition, a condition involving blood platelet aggregation, or an inflammatory condition. The present invention further provides a compound of formula (I), or a pharmaceutically acceptable salt, solvate, ester, or amide thereof for use in the prophylaxis or treatment of septic shock. The present invention still further provides a compound of formula (I), or a pharmaceutically acceptable salt, solvate, ester or amide thereof for use in the prophylaxis or treatment of neurodegeneration or dementia associated with HIV infection.

The amount of a compound of formula (I) or pharmaceutically acceptable salt, solvate, ester or amide thereof, which is required to achieve the desired biological effect will depend on a number of factors such as the use for which it is intended, the means of administration, and the recipient. A typical daily dose for the treatment of septic shock, for instance, may be expected to lie in the range of 0.005 mg/kg–100 mg/kg, preferably 0.5–100 mg/kg, and most preferably 0.5–20 mg/kg. This dose may be administered as a single unit dose or as several separate unit doses or as a continuous infusion. An intravenous dose may be expected to lie in the range of 0.0025 mg/kg to 200 mg/kg and would typically be administered as an infusion. Similar dosages would be applicable for the treatment of other disease states. For administration to the lungs of a subject by aerosol an amount of the compound should be used sufficient to achieve concentrations on the airway surface liquid of the subject of about 2 to 1000 µmol.

Thus, in a further aspect of the present invention, there are provided pharmaceutical compositions comprising, as active ingredient, a compound of formula (I) or a pharmaceutically acceptable salt, solvate, ester, or amide thereof, together with at least one pharmaceutical carrier or recipient. These pharmaceutical compositions may be used in the prophylaxis and treatment of conditions such as septic shock, and allergic or inflammatory conditions as well as in neurodegeneration and dementia associated with HIV infection. The carrier must be pharmaceutically acceptable to the recipient and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredients. If desired other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the condition being treated and on the nature of the active compound, but where possible, iv administration is preferred for the treatment of Septic Shock, for instance. For the treatment of a condition such as asthma, however, oral or inhalation, would be the preferred route of administration.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an innert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof. The active ingredient is typically present in such formulations at a concentration of from 0.1 to 15% w/w.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Aqueous solutions, are typically prepared by dissolving the active ingredient in saline to which cyclodextrin has been added.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5–10 µm, preferably 1–5 µm, to ensure delivery into the bronchial tree. For nasal administration, a particle size in the range 10–500 µm is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas through a narrow venturi orifice, typically air or oxygen, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of for example, sodium chloride. Optional additives include preservatives if the formulation is not prepared sterile, for example, methyl hydroxy-benzoate, anti-oxidants, flavouring agents, volatile oils, buffering agents and surfactants.

Suitable formulations for administration by insulation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

Therefore, according to a further aspect of the present invention, there is provided the use of a compound of formula (I) or a pharmaceutically acceptable salt, solvate, ester, or amide thereof in the preparation of a medicament for the prophylaxis or treatment of a clinical condition for which an inhibitor of one or more of arachidonate 5-lipoxygenase, arachidonate cyclooxygenase, or lyso-PAF:acetyl-CoA acetyltransferase is indicated; for example a spasmogenic condition, an allergic condition, a condition involving blood platelet aggregation, or an inflammatory condition. The present invention also provides use of a compound of formula (I) or a pharmaceutically acceptable salt, solvate, ester or amide thereof in the preparation of a medicament for the prophylaxis or treatment of septic shock, neurodegeneration or dementia associated with HIV infection.

Compounds according to the invention can be made according to the methods analogous to those described in EP-B-0203721 and the corresponding U.S. Pat. No. 5,015,647. Therefore, according to a further aspect of the invention, there is provided a process for preparing the compounds of formula (I), or salts, solvates, or pharmaceutically acceptable esters or amides thereof which comprises cyclising a compound of formula (II)

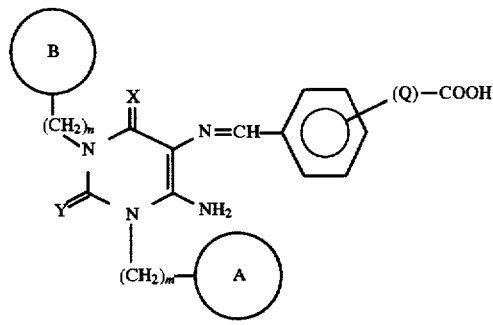

(II)

wherein A, B, m, n, X, Y, and Q are as defined for the compound of formula (I), for example by treatment with an oxidant such as iodine;

and optionally converting the compound of formula (I) so formed to a different compound of formula (I) or to a corresponding salt, solvate, or pharmaceutically acceptable ester or amide.

Compounds of formula (II) may be obtained by reaction of a compound of formula (III)

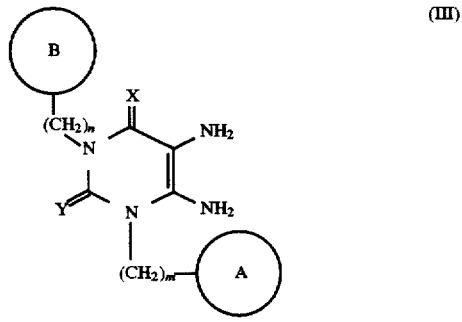

(III)

wherein A, B, m, n, X, and Y are as defined for the compound of formula (I), with a compound of formula (IV)

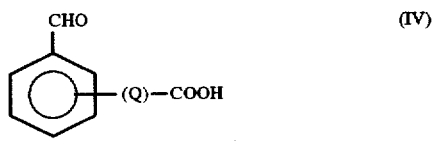

(IV)

wherein Q is as defined for the compound of formula (I), suitably in a polar solvent at non-extreme temperature.

As would be understood by a person skilled in the art, the compound of formula (II) need not necessarily be isolated before conversion to the corresponding compound of formula (I).

Compounds of formula (III) may be prepared from the corresponding 5-nitroso compound (V)

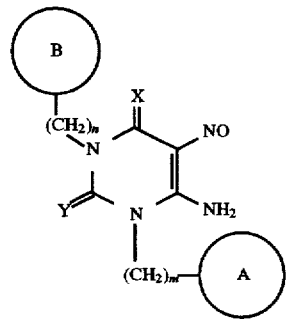

(V)

by standard reduction techniques, for example treatment with hydrogen in the presence of a suitable catalyst, such as palladium on carbon.

Compounds of formula (V) may be prepared according to the methods of EP 0203721.

Compounds of formula (IV) are commercially available or may be obtained by methods known to a person skilled in the art.

Conversion of a compound of formula (I) to a salt, solvate, or pharmaceutically acceptable ester or amide thereof may be effected by standard methods known to a person skilled in the art.

The invention will now be described by way of illustration only, by the following examples:

EXAMPLE 1

(E)-4-[1,3 Bis(cyclohexylmethyl)-1,2,3,6-tetrahydro-2,6-dioxo-9H-purin-8-yl]cinnamic Acid (a) 1,3-Bis(cyclohexylmethyl)urea A mixture of cyclohexanemethylamine (Aldrich, 68.66 g, 0.607 mole) and 5N sodium hydroxide (Fisher, 200 mL) was stirred vigorously with cooling (−10° C.) while a solution of phosgene (30.0 g, 0.303 mole) in toluene (600 mL) was added rapidly. After stirring for 20 minutes, the resulting mixture was filtered and the precipitated solid was washed with water (~1500 mL) and dried (0.5 Torr) to give 1,3-bis(cyclohexylurea) as white powder (72.72 g, 95%), m.p. 150°–152° C.;

$^1$H-NMR (DMSO-$d_6$) δ: 5.74 (br t, J=5.8 Hz, 2, 2 NH), 2.81 (t, J=6.3 Hz, 4, 2 NCH$_2$), 1.62, 1.25, and 0.85 (all m, 22, 2 cyclohexyl). Anal. Calcd for $C_{15}H_{28}N_2O$: C, 71.38; H, 11.18; N, 11.10. Found: C, 71.22; H, 11.17; N, 11.15.

(b) 6-Amino-1,3-bis(cyclohexylmethyl)uracil

Cyanoacetic acid (Aldrich, 21.0 g, 0.247 mole) was dissolved in acetic anhydride (260 mL). This solution was added to 1,3-bis(cyclohexylmethyl)urea (from step (a), 54.5 g, 0.216 mole) and the solution maintained at 80° C. for 2 h under nitrogen. Volatiles were removed in vacuo and the residual oil dried by evaporation of portions of 10% water-ethanol (3×400 mL). The residual solids were dissolved in ethanol (600 mL)-water(300 mL) at 80° C. with adjustment of the pH to 10 by addition of 10% aqueous sodium carbonate. The hot solution was diluted with water (75 mL) and cooled to ambient temperature. The colorless crystals which formed were filtered off, washed with water (3×500 mL) and dried at 0.5 Torr to give 6-amino-1,3-bis(cyclohexylmethyl)uracil (64.98 g, 94%), m.p. 138°–141° C.;

$^1$H-NMR (DMSO-$d_6$) δ: 6.73 (br s, 2, NH$_2$), 4.63 (s, 1, H-5), 3.67 (d, J=7.3 Hz, 2, NCH$_2$), 3.57 (d, J=7.3 Hz, 2, NCH$_2$), 1.55 and 1.09 (both m, 22, 2 cyclohexyl). Anal. Calcd for $C_{18}H_{29}N_3O_2 \cdot H_2O$: C, 64.07; H, 9.26; N, 12.45. Found: C, 63.98; H, 9.27; N, 12.48.

(c) 6-Amino-1,3-bis(cyclohexylmethyl)-5-nitrosouracil

6-Amino-1,3-bis(cyclohexylmethyl)uracil (from step (b), 25.0 g, 78.3 mmol) was dissolved in glacial acetic acid (440 mL), water (440 mL) and ethanol (440 mL) at reflux. To this solution was added sodium nitrite (5.65 g, 81.9 mequiv). The resulting mixture was stirred as it cooled slowly to ambient temperature. The lavender precipitate was filtered off, washed with 1:1 water-ethanol and dried to give 6-amino-1,3-bis(cyclohexylmethyl)-5-nitrosouracil as light purple crystals (23.46 g, 86%), m.p. 240°–243° C. dec with effervescence;

$^1$H-NMR (DMSO-d$_6$) δ: 13.23 (br s, 1, =NOH), 9.00 (br s, 1, =NH), 3.73 (br t, J=6.86, 4, 2 NCH$_2$), 2.0–1.6 and 1.7–1.1 (both m, total 22, 2 cyclohexyl). Anal. Calcd for C$_{18}$H$_{28}$N$_4$O$_3$: C, 62.05; H, 8.10; N, 16.08. Found: C, 62.13; H, 8.12; N, 16.03.

(d) (E)-4-|1,3 Bis(cyclohexylmethyl)-1,2,3,6-tetrahydro-2,6-dioxo-9H-purin-8-yl|-cinnamic acid The title compound was prepared from 1,3-bis(cyclohexylmethyl)-5,6-diaminouracil by the method of J. Perutmattam, Syn. Commun. 1989, 19:3367–3370. 1,3-Bis(cyclohexylmethyl)-5,6-diaminouracil was freshly prepared by shaking a mixture of 6-amino 1,3-bis(cyclohexylmethyl)-5-nitrosouracil (from step (c), 5.00 g, 14.35 mmol) in methanol (250 mL)-water (25 mL) with 10% palladium on carbon (0.50 g) under hydrogen (50 psi) on a Parr shaker for 2 h. The catalyst was filtered off (Celite) and the colorless filtrate was concentrated to 25 mL. 4-Formylcinnamic acid (Aldrich, 2.53 g, 14.35 mmol) was added to this solution of 1,3-bis(cyclohexylmethyl)-5,6-diaminouracil and the resulting yellow mixture was concentrated and the residual yellow solid dried by evaporation of several portions of absolute ethanol. The resulting yellow powder (Schiff base intermediate) was stirred in dimethoxyethane (115 mL) with iodine (4.0 g, 15.7 mequiv) at 60° C. (oil bath) for 20 h. A saturated aqueous solution of sodium thiosulfate was added to the warm reaction mixture until complete decolorization of iodine resulted. The pale yellow precipitate was filtered off, washed with water, and dried at 0.5 Torr to give (E)-4-|1,3 bis(cyclohexylmethyl)-1,2,3,6-tetrahydro-2,6-dioxo-9H-purin-8-yl|cinnamic acid as a pale yellow powder (6.73 g, 91%), m.p. >300° C. Such samples were further purified by dissolving them in 1N aqueous sodium hydroxide, filtering the resulting hazy solution through Celite, and acidifying the clear filtrate with hydrochloric acid. The resulting precipitate was filtered and washed with water to give title compound as a pale yellow powder, m.p. >300° C.;

$^1$H-NMR (DMSO-d$_6$) δ: 13.80 and 12.40 (both br m, 1 each, CO$_2$H and NH), 8.12 (d, J=8.3 Hz, 2, 2 phenyl CH), 7.84 (d, J=8.4 Hz, 2, 2 phenyl CH), 7.64 (d, J=16.0 Hz, 1, CH=), 6.64 (d, J=16.0 Hz, 1, CH=), 3.93 (d, J=7.0 Hz, 2, CH$_2$N), 3.79 (d, J=6.8 Hz, 2, CH$_2$N), 2.0–1.4 and 1.3–0.85 (both br m, 22 total, 2 cyclohexyl). Anal. Calcd for C$_{28}$H$_{34}$N$_4$O$_4$: C, 68.55; H, 6.99; N, 11.42. Found: C, 68.45; H, 6.98; N, 11.48.

EXAMPLE 2

Sodium (E)-4-|1,3 Bis(cyclohexylmethyl)-1,2,3,6-tetrahydro-2,6-dioxo-9H-purin-8-yl|-cinnamate (E)-4-|1,3 Bis(cyclohexylmethyl)-1,2,3,6-tetrahydro-2,6-dioxo-9H-purin-8-yl|cinnamic acid (Example 1) was slurried in refluxing ethanol-water with one equivalent of 1N aqueous sodium hydroxide. The hot mixture was filtered and the filtrate allowed to cool slowly to ambient temperature. The precipitate which formed was filtered, slurried in 95% ethanol, and dried to give the sodium salt of (E)-4-|1,3bis(cyclohexylmethyl)-1,2,3,6-tetrahydro-2,6-dioxo-9H-purin-8-yl|cinnamic acid as a pale yellow powder, m.p. >300° C.; $^1$H-NMR (DMSO-d$_6$) consistent with structure.

Anal. Calcd for C$_{28}$H$_{33}$N$_4$O$_4$Na: C, 63.49; H, 6.64; N, 10.58; Na, 4.34. Found: C, 63.48; H, 6.63; N, 10.63; Na, 4.36.

EXAMPLE 3

(E)-Methyl-4-|1,3-bis(cyclohexylmethyl)-1,2,3,6-tetrahydro-2,6-dioxo-9H-purin-8-yl|cinnamate (a) (E)-Methyl 4-(dimethoxymethyl)cinnamate 4-Formylcinnamic acid dimethyl acetal (Cleeland, Jr., et al., U.S. Pat. No. 3,969,373; Jul. 13, 1976) (20.00 g, 90.00 mmol) and anhydrous potassium carbonate (12.44 g, 90.00 mmol) were stirred in anhydrous DMF (189 mL) for 5 minutes. Methyl iodide (12.8 g, 90.0 mmol) was added and the resulting mixture was stirred vigorously with gentle heating (oil bath at 40° C.) for 18 h. Volatiles were evaporated in vacuo and the residue partitioned between hexanes (400 mL) and water (100 mL). The hexanes layer was dried (magnesium sulfate) and evaporated to give (E)-methyl 4-(dimethoxymethyl)cinnamate as a pale yellow oil (18.98 g, 89%);

$^1$H-NMR (DMSO-d$_6$) consistent with structure. Anal. Calcd for C$_{13}$H$_{16}$O$_4$: C, 66.09; H, 6.83. Found: C, 65.96; H, 6.86.

(b) (E)-Methyl 4-|1,3-bis(cyclohexylmethyl)-1,2,3,6-tetrahydro-2,6-dioxo-9H-purin-8-yl|cinnamate (E)-Methyl 4-(dimethoxymethyl)cinnamate (from step (a)) was used in place of 4-formylcinnamic acid in the procedure described in step (d) of Example 1, except that a drop of acetic acid was added during the formation of the Schiff base with 1,3-bis(cyclohexylmethyl)-5,6-diaminouracil. Title compound was formed as a white powder, m.p. >270° C.; $^1$H-NMR (DMSO-d$_6$) consistent with structure.

Anal. Calcd for C$_{29}$H$_{36}$N$_4$O$_4$: C, 69.02; H, 7.19; N, 11.10. Found: C, 68.97; H, 7.19; N, 11.21.

EXAMPLE 4

(E)-4-|1,3 Bis(cyclopentylmethyl)-1,2,3,6-tetrahydro-2,6-dioxo-9H-purin-8-yl|cinnamic Acid (a) 1,3-Bis(cyclopentylmethyl)urea In the manner of step (a) of Example 1, cyclopentanemethylamine (K. Jewers and J. McKenna, J. Chem. Soc. 1958, 2209–2217; 23.0 g, 0.158 mole) was reacted with phosgene to give 1,3-bis(cyclopentylmethyl)urea as white powder (14.41 g, 81%), m.p. 162°–164° C.;

$^1$H-NMR (DMSO-d$_6$) consistent with structure. Anal. Calcd for C$_{13}$H$_{24}$N$_2$O.0.1 H$_2$O: C, 69.07; H, 10.79; N, 12.39. Found: C, 68.96; H, 10.66; N, 12.37.

(b) 6-Amino-1,3-bis(cyclopentylmethyl)uracil

In the manner of step (b) of Example 1, 1,3-bis(cyclopentylmethyl)urea (from step (a), 14.00 g, 61.91 mmol) was converted to 6-amino-1,3-bis(cyclopentylmethyl)uracil (16.93 g, 94%), m.p. 169°–170° C.;

$^1$H-NMR (DMSO-d$_6$) consistent with structure. Anal. Calcd for C$_{16}$H$_{25}$N$_3$O$_2$.0.75 H$_2$O: C, 63.03; H, 8.76; N, 13.78. Found: C, 63.02; H, 8.79; N, 13.80.

(c) 6-Amino-1,3-bis(cyclopentylmethyl)-5-nitrosouracil

In the manner of step (c) of Example 1, 6-amino-1,3-bis(cyclopentylmethyl)uracil (from step (b), 16.66 g, 57.17 mmol) was converted to 6-amino-1,3-bis(cyclopentylmethyl)-5-nitrosouracil, isolated as purple flakes (15.89 g, 87%), m.p. 254.5°–255° C.;

¹H-NMR (DMSO-d₆) consistent with structure. Anal. Calcd for C₁₆H₂₄N₄O₃: C, 59.98; H, 7.55; N, 17.49. Found: C, 59.92; H, 7.50; N, 17.53.

(d) (E)-4-[1,3 Bis(cyclopentylmethyl)-1,2,3,6-tetrahydro-2,6-dioxo-9H-purin-8-yl]cinnamic acid In the manner of step (d) of Example 1, 6-amino-1,3-bis(cyclopentylmethyl)-5-nitrosouracil (from step (c), 3.00 g, 9.36 mmol) was converted to (E)-4-[1,3 bis(cyclopentylmethyl)-1,2,3,6-tetrahydro-2,6-dioxo-9H-purin-8-yl]cinnamic acid, isolated as a yellow powder (3.700 g, 86%), m.p. >300° C.; ¹H-NMR (DMSO-d₆) consistent with structure.

Anal. Calcd for C₂₆H₃₀N₄O₄: C, 67.51; H, 6.54; N, 12.11. Found: C, 67.55; H, 6.59; N, 12.15.

EXAMPLE 5

(E)-4-[1,3 Bis(cyclobutylmethyl)-1,2,3,6-tetrahydro-2,6-dioxo-9H-purin-8-yl]cinnamic Acid (a) 1,3-Bis(cyclobutylmethyl)urea In the manner of step (a) of Example 1, cyclobutanemethylamine hydrochloride (Buchman and Howton, J. Amer. Chem. Soc. 1948, 70:2517; 7.96 g, 80.5 mmol) was reacted with phosgene to give 1,3-bis(cyclobutylmethyl)urea as white powder (5.20 g, 37%), m.p. 153°–155° C.; ¹H-NMR (DMSO-d₆) consistent with structure.

Anal. Calcd for C₁₁H₂₀N₂O: C, 67.31; H, 10.27; N, 14.27. Found: C, 67.19; H, 10.23; N, 14.20.

(b) 6-Amino-1,3-bis(cyclobutylmethyl)uracil

In the manner of step (b) of Example 1, 1,3-bis(cyclobutylmethyl)urea (from step (a), 5.00 g, 25.5 mmol) was converted to 6-amino-1,3-bis(cyclobutylmethyl)uracil (6.02 g, 90%), m.p. 89°–90° C.; ¹H-NMR (DMSO-d₆) consistent with structure.

Anal. Calcd for C₁₄H₂₁N₃O₂.0.45 H₂O: C, 61.95; H, 8.13; N, 15.48. Found: C, 62.00; H, 8.08; N, 15.47.

(c) 6-Amino-1,3-bis(cyclobutylmethyl)-5-nitrosouracil

In the manner of step (c) of Example 1, 6-amino-1,3-bis(cyclobutylmethyl)uracil (from step (b), 5.75 g, 21.8 mmol) was converted to 6-amino-1,3-bis(cyclopentylmethyl)-5-nitrosouracil, isolated as purple flakes (5.60 g, 88%), m.p. 251°–252° C.; ¹H-NMR (DMSO-d₆) consistent with structure.

Anal. Calcd for C₁₄H₂₀N₄O₃: C, 57.52; H, 6.90; N, 19.17. Found: C, 57.57; H, 6.91; N, 19.17.

(d) (E)-4-[1,3 Bis(cyclobutylmethyl)-1,2,3,6-tetrahydro-2,6-dioxo-9H-purin-8-yl]cinnamic acid In the manner of step (d) of Example 1, 6-amino-1,3-bis(cyclobutylmethyl)-5-nitrosouracil (from step (c), 3.00 g, 10.3 mmol) was converted to (E)-4-[1,3 bis(cyclobutylmethyl)-1,2,3,6-tetrahydro-2,6-dioxo-9H-purin-8-yl]cinnamic acid, isolated as a yellow powder (1.50 g, 33%), m.p. >300° C.; ¹H-NMR (DMSO-d₆) consistent with structure.

Anal. Calcd for C₂₄H₂₆N₄O₄.0.5 H₂O: C, 65.00; H, 6.14; N, 12.63. Found: C, 64.93; H, 6.11; N, 12.64.

EXAMPLE 6

(E)-4-[1,3 Bis(cyclopropylmethyl)-1,2,3,6-tetrahydro-2,6-dioxo-9H-purin-8-yl]cinnamic Acid (a) 1,3-Bis(cyclopropylmethyl)urea Cyclopropanemethylamine hydrochloride (Aldrich, 1.00 g, 9.30 mmol) and triethylamine (0.95 g, 9.39 mmol) were dissolved in chloroform (10 mL). 1,1'-Carbonyldiimidazole (Aldrich, 0.754 g, 4.65 mmol) was added and the resulting solution maintained at ~55° C. for 22 h. The chloroform solution was extracted with 1N hydrochloric acid (2×50 mL) and then with water (50 mL) and dried. Evaporation of the chloroform gave crude product (650 mg) which was recrystallized from toluene to give 1,3-bis(cyclopropylmethyl)urea as white crystals (462 mg, 59%), m.p. 127°–130° C.; ¹H-NMR (DMSO-d₆) consistent with structure.

Anal. Calcd for C₉H₁₆N₂O: C, 64.25; H, 9.59; N, 16.65. Found: C, 64.34; H, 9.57; N, 16.70.

(b) 6-Amino-1,3-bis(cyclopropylmethyl)uracil

In the manner of step (b) of Example 1, 1,3-bis(cyclopropylmethyl)urea (from step (a), 14.39 g, 85.53 mmol) was converted to 6-amino-1,3-bis(cyclopropylmethyl)uracil (16.35 g, 75%), m.p. 161°–165° C.; ¹H-NMR (DMSO-d₆) consistent with structure.

Anal. Calcd for C₁₄H₂₁N₃O₂.H₂O: C, 56.90; H, 7.56; N, 16.59. Found: C, 57.04; H, 7.62; N, 16.65.

(c) 6-Amino-1,3-bis(cyclopropylmethyl)-5-nitrosouracil

In the manner of step (c) of Example 1, 6-amino-1,3-bis(cyclopropylmethyl)uracil (from step (b), 14.44 g, 61.37 mmol) was nitrosated to 6-amino-1,3-bis(cyclopropylmethyl)-5-nitrosouracil, isolated as dark pink crystals (15.22 g, 94%), m.p. 228.5°–229° C. with dec.; ¹H-NMR (DMSO-d₆) consistent with structure.

Anal. Calcd for C₁₂H₁₆N₄O₃: C, 54.54; H, 6.10; N, 21.20. Found: C, 54.64; H, 6.12; N, 21.23.

(d) (E)-4-[1,3 Bis(cyclopropylmethyl)-1,2,3,6-tetrahydro-2,6-dioxo-9H-purin-8-yl]cinnamic acid In the manner of step (d) of Example 1, 6-amino-1,3-bis(cyclopropylmethyl)-5-nitrosouracil (from step (c), 2.00 g, 7.57 mmol) was converted to (E)-4-[1,3 bis(cyclopropylmethyl)-1,2,3,6-tetrahydro-2,6-dioxo-9H-purin-8-yl]cinnamic acid, isolated as a pale yellow powder (2.62 g, 86%), m.p. >250° C.; ¹H-NMR (DMSO-d₆) consistent with structure.

Anal. Calcd for C₂₂H₂₂N₄O₄: C, 65.01; H, 5.46; N, 13.78. Found: C, 65.14; H, 5.52; N, 13.68.

EXAMPLE 7

(E)-4-[1,3 Bis(cycloheptylmethyl)-1,2,3,6-tetrahydro-2,6-dioxo-9H-purin-8-yl]cinnamic Acid (a) 1,3-Bis(cycloheptylmethyl)urea In the manner of step (a) of Example 6, cycloheptanemethylamine hydrochloride (R. B. Turner and R. H. Garner, J. Amer. Chem. Soc. 1958, 80:1424–1430; 22.00 g, 0.135 mole) was reacted with 1,1'-carbonyldiimidazole to give 1,3-bis(cycloheptylmethyl)urea as a white powder (4.45 g, 24%), m.p. 106°–108° C.; ¹H-NMR (DMSO-d₆) consistent with structure.

Anal. Calcd for C₁₇H₃₂N₂O: C, 72.81; H, 11.50; N, 9.99. Found: C, 72.59; H, 11.48; N, 9.96.

(b) 6-Amino-1,3-bis(cycloheptylmethyl)uracil

In the manner of step (b) of Example 1, 1,3-bis(cycloheptylmethyl)urea (from step (a), 3.99 g, 14.23 mmol) was converted to 6-amino-1,3-bis(cyclopentylmethyl)uracil (3.22 g, 65%), m.p. 194°–197° C.; ¹H-NMR (DMSO-d₆) consistent with structure.

Anal. Calcd for C₂₀H₃₃N₃O₂.H₂O: C, 65.72; H, 9.65; N, 11.50. Found: C, 65.71; H, 9.63; N, 11.59.

(c) 6-Amino-1,3-bis(cycloheptylmethyl)-5-nitrosouracil

In the manner of step (c) of Example 1, 6-amino-1,3-bis(cycloheptylmethyl)uracil (from step (b), 2.97 g, 8.55 mmol) was converted to 6-amino-1,3-bis(cycloheptylmethyl)-5-nitrosouracil, isolated as a purple solid (2.80 g 87%), m.p. >250° C.; ¹H-NMR (DMSO-d₆) consistent with structure.

Anal. Calcd for C₂₀H₃₂N₄O₃: C, 63.80; H, 8.57; N, 14.88. Found: C, 63.81; H, 8.56; N, 14.81.

(d) (E)-4-[1,3 Bis(cycloheptylethyl)-1,2,3,6-tetrahydro-2,6-dioxo-9H-purin-8-yl]cinnamic acid In the manner of step (d) of Example 1, 6-amino-1,3-bis(cycloheptylmethyl)-5-nitrosouracil (from step (c), 2.45 g, 6.51 mmol) was converted to (E)-4-[1,3 bis(cycloheptylmethyl)-1,2,3,6-tetrahydro-2,6-dioxo-9H-purin-8-yl]cinnamic acid, isolated as a yellow powder (2.89 g, 86%), m.p. >250° C.; $^1$H-NMR (DMSO-$d_6$) consistent with structure.

Anal. Calcd for $C_{30}H_{38}N_4O_4 \cdot 0.35\ H_2O$: C, 68.64; H, 7.43; N, 10.67. Found: C, 68.61; H, 7.33; N, 10.71.

EXAMPLE 8

(E)-4-{1,3 Bis[2-(1-cyclohexen-1-yl)ethyl]-1,2,3,6-tetrahydro-2,6-dioxo-9H-purin-8-yl}cinnamic Acid (a) 1,3-Bis[2-(1-cyclohexen-1-yl)ethyl]urea In the manner of step (a) of Example 6, 2-(1-cyclohexenyl)ethylamine (Aldrich, 94.6 g, 0.733 mole as 97%) was reacted with 1,1'-carbonyldiimidazole to give 1,3-bis[2-(1-cyclohexen-1-yl)ethyl]urea as a white powder (56.26 g, 54%), m.p. 129°–131° C.;

$^1$H-NMR (DMSO-$d_6$) δ 5.47 (br s, 2, 2=CH), 4.23 (br s, 2, 2 NH), 3.22 (t, J=6.7 Hz, 4,2 CH$_2$N); 2.13 (t, J=6.7 Hz, 4, 2 CH$_2$C=), 1.99 and 1.92 (both m, 4 each, 4 C H$_2$CH=), 1.59 (m, 8, 4 CH$_2$). Anal. Calcd for $C_{17}H_{28}N_2O$: C, 73.87; H, 10.21; N10.13. Found: C, 73.91; H, 10.24; N, 10.18.

(b) 6-Amino-1,3-bis[2-(cyclohexen-1-yl)ethyl]uracil

In the manner of step (b) of Example 1, 1,3-bis[2-(1-cyclohexen-1-yl)ethyl]urea (from step (a), 55.00 g, 0.199 mol) was converted to 6-amino-1,3-bis[(2-(cyclohexen-1-yl)ethyl]uracil, isolated as a white powder (58.03 g, 85%), m.p. 172°–174° C.;

$^1$H-NMR (DMSO-$d_6$) δ: 6.73 (s, 2, NH$_2$), 5.30 (m, 2, 2=CH), 4.64 (s, 1, H-5), 3.88 and 3.76 (both t, J=7.2 Hz, 2 each, 2 CH$_2$N), 2.15-1.8 and 1.6-1.4 (m, 20, 10 CH$_2$). Anal. Calcd for $C_{20}H_{29}N_3O_2$: C, 69.94; H, 8.51; N, 12.23. Found: C, 69.85; H, 8.55; N, 12.19.

(c) 6-Amino-1,3-bis[2-(cyclohexen-1-yl)ethyl]-5-nitrosouracil

In the manner of step (c) of Example 1, 6-amino-1,3-bis[2-(cyclohexen-1-yl)ethyl]uracil (from step (b), 25.00 g, 72.78 mmol) was converted to 6-amino-1,3-bis[2-(cyclohexen-1-yl)ethyl]-5-nitrosouracil, isolated as a dark pink powder (25.75 g, 95%), m.p. 220°–222° C., $^1$H-NMR (DMSO-$d_6$) δ: 13.18 and 9.18 (both br s, 1 each, NH and =NOH), 5.29 and 5.39 (both m, 1 each, 2 CH=), 3.97 (m, 4, 2 NCH$_2$), 2.14 and 1.95 (both m, 4 and 8, respectively, 6 CH$_2$C=), 1.48 (m, 8, 4 CH$_2$). Anal. Calcd for $C_{20}H_{28}N_4O_3$: C, 64.50; H, 7.58; N, 15.04. Found: C 64.58; H, 7.58; N, 15.06.

(d) (E)-4-{1,3 Bis[2-(1-cyclohexen-1-yl)ethyl]-1,2,3,6-tetrahydro-2,6-dioxo-9H-purin-8-yl}cinnamic acid 6-Amino-1,3-bis[2-(cyclohexen-1-yl)ethyl]-5-nitrosouracil (from step (c), 2.00 g, 5.37 mmol) was dissolved in refluxing ethanol (33 mL)-water (50 mL). Ammonium sulfide (22% in water, 8 mL, ~26 mequiv) was added and the solution was maintained at ~70° C. for 4 h. The precipitated solid was filtered off, washed with water, dried and then converted as in step (d) of Example 1 to (E)-4-{1,3 bis[2-(1-cyclohexen-1-yl)ethyl]-1,2,3,6-tetrahydro-2,6-dioxo-9H-purin-8-yl}cinnamic acid, isolated as a yellow powder (1.80 g, 65%), m.p. >250° C.;

$^1$H-NMR (DMSO-$d_6$) d: 13.94 (br s, 1, CO$_2$H), 12.52 (br s, 1, NH), 7.86 and 8.17 (both d, J=8.3 Hz, C$_6$H$_4$), 7.64 and 6.65 (both d, J=16 H, 1 each, CH=CHCO$_2$), 5.31 and 5.26 (both m, 1 each, 2 CH=), 4.14 and 4.00 (both m, 2 each, 2 CH$_2$N), 2.4-1.3 (m, 20, 10 CH$_2$). Anal. Calcd for $C_{30}H_{34}N_4O_4$: C, 70.02; H, 6.66; N, 10.89. Found: C, 69.77; H, 6.72; N, 10.80.

EXAMPLE 9

(E)-4-[1,3 Bis(2-cyclohexylethyl)-1,2,3,6-tetrahydro-2,6-dioxo-9H-purin-8-yl]cinnamic Acid (a) 1,3-Bis(2-cyclohexylethyl)urea 1,3-Bis[2-(1-cyclohexen-1-yl)ethyl]urea (from step (a) example 8, 10.82 g, 39.14 mmol) was dissolved in methanol (400 mL)-water (12 mL) and shaken with 10% palladium on carbon (600 mg) under hydrogen (55 psi) on a Parr apparatus for 7.5 h. The catalyst was filtered off (Celite) and volatiles were removed in vacuo to leave 1,3-bis(2-cyclohexylethyl)urea as white crystals (10.72 g, 98%), m.p. 150°–151.5° C.; $^1$H-NMR (DMSO-$d_6$) consistent with structure.

Anal. Calcd for $C_{17}H_{32}N_2O$: C, 72.81; H, 11.50; N9.99. Found: C, 72.74; H, 11.62; N, 9.97.

(b) 6-Amino-1,3-bis(2-cyclohexylethyl)uracil

In the manner of step (b) of Example 1, 1,3-bis(2-cyclohexylethyl)urea (from step (a), 12.79 g, 45.60 mmol) was converted to 6-amino-1,3-bis(2-cyclohexylethyl)uracil, isolated as a white powder (15.31 g, 97%), m.p. 146°–148° C.; $^1$H-NMR (DMSO-$d_6$) consistent with structure.

Anal. Calcd for $C_{20}H_{33}N_3O_2 \cdot 0.30\ H_2O$: C, 68.07; H, 9.60; N, 11.91. Found: C, 68.05; H, 9.61; N, 11.92.

(c) 6-Amino-1,3-bis(2-cyclohexylethyl)-5-nitrosouracil

In the manner of step (c) of Example 1, 6-amino-1,3-bis(2-cyclohexylethyl)uracil (from step (b), 15.10 g, 43.45 mmol) was converted to 6-amino-1,3-bis(2-cyclohexylethyl)-5-nitrosouracil, isolated as a purple powder (15.16 g, 93%), m.p. 231°–233° C.; $^1$H-NMR (DMSO-$d_6$) consistent with structure.

Anal. Calcd for $C_{20}H_{32}N_4O_3$: C, 63.80; H, 8.57; N, 14.88. Found: C 63.88; H, 8.57; N, 14.97.

(d) (E)-4-[1,3 Bis(2-cyclohexylethyl)-1,2,3,6-tetrahydro-2,6-dioxo-9H-purin-8-yl]cinnamic acid In the manner of step (d) of Example 1, 6-amino-1,3-bis(2-cyclohexylethyl)-5-nitrosouracil (from step (c), 2.49 g, 6.61 mmol) was converted to (E)-4-[1,3 bis(2-cyclohexylethyl)-1,2,3,6-tetrahydro-2,6-dioxo-9H-purin-8-yl]cinnamic acid, isolated as a pale yellow powder (3.00 g, 88%), m.p. >250° C.; $^1$H-NMR (DMSO-$d_6$) consistent with structure.

Anal. Calcd for $C_{30}H_{38}N_4O_4$: C, 69.47; H, 7.38; N, 10.80. Found: C, 69.32; H, 7.36; N, 10.76.

EXAMPLE 10

4-[1,3 Bis(cyclohexylmethyl)-1,2,3,6-tetrahydro-2,6-dioxo-9H-purin-8-yl]benzoic Acid The title compound was prepared from 1,3-bis(cyclohexylmethyl)-5,6-aminouracil by the method of J. Perutmattam, Syn. Commun. 1989, 19:3367–3370. 1,3-Bis(cyclohexylmethyl)-5,6-diaminouracil was freshly prepared by shaking a mixture of 6-amino-1,3-bis(cyclohexylmethyl)-5-nitrosouracil (from step (c) example 1, 2.00 g, 5.74 mmol) in methanol (250 mL)-water (25 mL) with 10% palladium on carbon (0.20 g) under hydrogen (40 psi) on a Parr shaker for 2 h. The catalyst was filtered off (Celite) and the colorless filtrate was concentrated to 50 mL. 4-Carboxybenzaldehyde (Aldrich, 860 mg, 5.73 mmol) was added to this solution of 1,3-bis(cyclohexylmethyl)-5,6-diaminouracil. The resulting yellow mixture was concentrated and the residual yellow solid dried by evaporation of several portions of absolute ethanol. The yellow powder (Schiff base) was then stirred in dimethoxyethane (80 mL) with iodine (1.6 g, 6.30 mequiv) at 60° C. (oil bath) for 24 h. A saturated aqueous solution of sodium thiosulfate (~15 mL) was added to the warm reaction mixture until complete decolorization of iodine resulted. The pale yellow precipitate was filtered off, washed with water, and dried at 0.5 Torr to give 4-[1,3 bis(cyclohexylmethyl)- 1,2,3,6-tetrahydro-2,6-dioxo-9H-purin-8-yl]benzoic acid as a pale yellow powder (2.13 g, 80%), m.p. >300° C.; $^1$H-NMR (DMSO-$d_6$) consistent with structure.

Anal. Calcd for $C_{26}H_{32}N_4O_4 \cdot 0.25 \; H_2O$: C, 66.58; H, 6.98; N, 11.94. Found: C, 66.62; H, 6.98; N, 11.94.

EXAMPLE 11

3-{4-[1,3 Bis(cyclohexylmethyl)-1,2,3,6-tetrahydro-2,6-dioxo-9H-purin-8-yl]phenyl}propionic Acid (E)-4-[1,3 Bis(cyclohexylmethyl)-1,2,3,6-tetrahydro-2,6-dioxo-9H-purin-8-yl]cinnamic acid (from step (d) example 1, 560 mg, 1.13 mmol) was shaken with 10% palladium on carbon (500 mg) in DMF (100 mL) under hydrogen (30 psi) in a Parr apparatus for 6 h. Catalyst was filtered off (Celite) and volatiles evaporated in vacuo. The residual oil was solidified from DMF, filtered, dissolved in 1N sodium hydroxide, and then reprecipitated by addition of excess 1N hydrochloric acid. Such a sample was filtered, washed with water and dried to give title compound as a white powder, m.p. >300° C.; $^1$H-NMR (DMSO-$d_6$) consistent with structure.

Anal. Calcd for $C_{28}H_{36}N_4O_4 \cdot 0.25 \; H_2O$: C, 67.65; H, 7.40; N, 11.27. Found: C, 67.60; H, 7.33; N, 11.28.

EXAMPLE 12

(E)-4-[3(Cyclohexylmethyl)-1,2,3,6-tetrahydro-2,6-dioxo-1-propyl-9H-purin-8-yl]cinnamic Acid (a) 1-(Cyclohexylmethyl)-3-propylurea Propyl isocyanate (Aldrich, 42 mL, 0.442 mol) was added dropwise to a solution of cyclohexanemethylamine (Aldrich, 50.1 g, 0.442 mol) in anhydrous benzene (800 mL) at 0° C. under nitrogen. The solution was then stirred for 15 min before being concentrated in vacuo to a volume of 250 mL. The colorless crystals which formed upon standing at 0° C. were filtered off, washed with hexanes (2×70 mL), and dried (0.5 Torr) to give 1-(cyclohexylmethyl)-3-propylurea (83.90 g, 96%), m.p. 60°–61° C.; $^1$H-NMR (DMSO-$d_6$) consistent with structure.

Anal. Calcd for $C_{11}H_{22}N_2O$: C, 66.62; H, 11.18; N, 14.13. Found: C, 66.61; H, 11.12; N, 14.22.

(b) 6-Amino-1-(cyclohexylmethyl)-3-propyluracil

In the manner of step (b) of Example 1, 1-(cyclohexylmethyl)-3-propylurea (from step (a), 62.45 g, 0.315 mol) was converted to a mixture of 6-amino-1-(cyclohexylmethyl)-3-propyluracil and 6-amino-3-(cyclohexylmethyl)-1-propyluracil. Fractional crystallization of this mixture from ethanol (400 mL)-water (400 mL), followed by recrystallization from ethanol(150 mL)-water (50 mL), and drying (0.5 Torr) provided 6-amino-1-(cyclohexylmethyl)-3-propyluracil as a white crystalline solid (43.046 g, 48%), m.p. >110° C. (sublimes); $^1$H-NMR (DMSO-$d_6$) consistent with structure.

Anal. Calcd for $C_{14}H_{23}N_3O_2 \cdot 0.90 \; H_2O \cdot 0.05 \; C_2H_6O$: C, 59.66; H, 8.91; N, 14.80. Found: C, 59.67; H, 9.01; N, 14.84.

The mother liquors provided a 50:50 mixture of the regional isomers (ca 50 g, ca 50%).

(c) 6-Amino-1-(cyclohexylmethyl)-3-propyl-5-nitrosouracil

In the manner of step (c) of Example 1, 6-amino-1-(cyclohexylmethyl)-3-propyluracil (from step (b), 42.24 g, 159 mmol) was converted to 6-amino-1-(cyclohexylmethyl)-3-propyl-5-nitrosouracil isolated as a pink powder (38.88 g, 83%), m.p. 231°–233° C.; $^1$H-NMR (DMSO-$d_6$) consistent with structure.

Anal. Calcd for $C_{14}H_{22}N_4O_3$: C, 57.13; H, 7.53; N, 19.03. Found: C 57.19; H, 7.58; N, 19.09.

(d) (E)-4-[3-(Cyclohexylmethyl)-1,2,3,6-tetrahydro-2,6-dioxo-1-propyl-9H-purin-8-yl]cinnamic acid In the manner of step (d) of Example 1, 6-amino-1-(cyclohexylmethyl)-3-propyl-5-nitrosouracil (from step (c), 5.89 g, 20.0 mmol) was converted to (E)-4-[3-(cyclohexylmethyl)-1,2,3,6-tetrahydro-2,6-dioxo-1-propyl-9H-purin-8-yl]cinnamic acid, isolated as a white powder (6.816 g, 77%), m.p. >350° C.; $^1$H-NMR (DMSO-$d_6$) consistent with structure.

Anal. Calcd for $C_{24}H_{28}N_4O_4 \cdot 0.35 \; H_2O$: C, 65.10; H, 6.53; N, 12.65. Found: C, 65.08; H, 6.52; N, 12.58.

EXAMPLE 13

(E)-4-[1-(Cyclohexylmethyl)-1,2,3,6-tetrahydro-2,6-dioxo-3-propyl-9H-purin-8-yl]cinnamic Acid (a) 2-Cyano-N-(cyclohexylmethyl)acetamide 2-Cyano-N-(cyclohexylmethyl)acetamide was prepared by the method of V. Papesh, J. Org. Chem. 1951, 16, 1879–1889. Ethyl cyanoacetate (Aldrich, 18.41 mL, 173 mmol) was added to neat cyclohexanemethylamine (Aldrich, 19.585 g, 173 mmol), and the resulting solution was stirred for 2 h under nitrogen. At this time, the reaction mixture solidified. After standing for 18 h the white crystalline solid was broken up, filtered, washed with water (150 mL), and dried (0.1 Torr, 40° C.) to provide 2-cyano-N-(cyclohexylmethyl)acetamide (29.030 g, 93%), m.p. 83°–84° C.; $^1$H-NMR (DMSO-$d_6$) consistent with structure.

Anal. Calcd for $C_{10}H_{16}N_2O$: C, 66.63; H, 8.95; N, 15.54. Found: C, 66.67; H, 9.00; N, 15.62.

(b) 6-Amino-3-(cyclohexylmethyl)-1-propyluracil

6-Amino-3-(cyclohexylmethyl)-1-propyluracil was prepared by the method of V. Papesh, J. Org. Chem. 1951, 16, 1879–1889. A solution of propyl isocyanate (Aldrich, 10.92 mL, 116.5 mmol) and 2-cyano-N-(cyclohexylmethyl) acetamide (from step (a), 14.00 g, 77.7 mmol) in anhydrous toluene (100 mL) was stirred at reflux (heating mantle) under nitrogen for 24 h. Volatiles were then removed at 20 Torr and 50° C., and the resulting orange oil was chromatographed on silica gel. 1-(2-Cyanoacetyl)-1-cyclohexylmethyl-3-propylurea eluted with hexane/ethyl acetate (5:2) as a yellow oil, which solidified upon standing (2.708 g). Unreacted 2-cyano-N-(cyclohexylmethyl) acetamide eluted with hexane/ethylacetate (1:1) as a white crystalline solid (12.02 g), which was resubmitted to the reaction conditions described above. This process was repeated twice to provide 1-(2-cyanoacetyl)-1-cyclohexylmethyl-3-propylurea (total for the three runs: 7.101 g, 34%). $^1$H-NMR (DMSO-$d_6$) consistent with structure. Unreacted 2-cyano-N-(cyclohexylmethyl)acetamide was also recovered (7.108 g, 51%).

A slurry of 1-(2-cyanoacetyl)-1-cyclohexylmethyl-3-propylurea from above (7.10 g, 26.8 mmol) in water (45 mL)-ethanol (15 mL) was heated to 100° C. (oil bath), with adjustment of the pH to 10 by the addition of solid sodium carbonate. The resulting yellow solution was stirred for 1 h, during which time white crystalline solids formed. After 1 h 40 min, the mixture was cooled to 0° C. (icebath), and the white crystals were filtered off, washed with water (3×15 mL), and air-dried to provide 6-amino-3-(cyclohexylmethyl)-1-propyluracil as a slightly moist crystalline solid (8.85 g, quantitative yield). A small portion of this material was dried at 0.1 Torr to provide an analytically pure sample, m.p. 121°–122° C.; $^1$H-NMR (DMSO-$d_6$) consistent with structure.

Anal. Calcd for $C_{14}H_{23}N_3O_2$: C, 63.37; H, 8.74; N, 15.84. Found: C, 63.31; H, 8.77; N, 15.88.

(c) 6-Amino-3-(cyclohexylmethyl)-5-nitroso-1-propyluracil

In the manner of step (c) of Example 1, 6-amino-3-(cyclohexylmethyl)-1-propyluracil (from step (b), 8.14 g, 26 mmol) was nitrosated to 6-amino-3-(cyclohexylmethyl)-5-nitroso-1-propyluracil isolated as purple crystals (5.470 g, 72%), m.p. 225°–226° C. with dec.; $^1$H-NMR (DMSO-d$_6$) consistent with structure.

Anal. Calcd for C$_{14}$H$_{22}$N$_4$O$_3$: C, 57.13; H, 7.53; N, 19.03. Found: C, 57.04; H, 7.59; N, 18.95.

(d) (E)-4-[1-(Cyclohexylmethyl)-1,2,3,6-tetrahydro-2,6-dioxo-3-propyl-9H-purin-8-yl]cinnamic acid In the manner of step (d) of Example 1, 6-amino-3-(cyclohexylmethyl)-5-nitroso-1-propyluracil (from step (c), 2.354 g, 8.0 mmol) was converted to (E)-4-[1-(cyclohexylmethyl)-1,2,3,6-tetrahydro-2,6-dioxo-3-propyl-9H-purin-8-yl]cinnamic acid, isolated as a pale yellow powder (2.850 g, 81%), m.p. >350° C.; $^1$H-NMR (DMSO-d$_6$) consistent with structure.

Anal. Calcd for C$_{24}$H$_{28}$N$_4$O$_4$·0.30 H$_2$O: C, 65.23; H, 6.52; N, 12.68. Found: C, 65.21; H, 6.48; N, 12.58.

EXAMPLE 14

(E)-4-[3-Butyl-1-(cyclohexylmethyl)-1,2,3,6-tetrahydro-2,6-dioxo-9H-purin-8-yl]cinnamic Acid (a) 6-Amino-1-butyl-3-(cyclohexylmethyl)-5-nitrosouracil In the manner of step (b) of Example 13, 2-cyano-N-(cyclohexylmethyl)acetamide (from step (a) example 13, 14.00 g, 77.7 mmol) was condensed with butyl isocyanate (Aldrich, 13.12 mL, 116.5 mmol) to provide 1-butyl-3-(2-cyanoacetyl)-1-(cyclohexylmethyl)urea as a yellow oil (total for two runs: 5.005 g, 23%). $^1$H-NMR (DMSO-d$_6$) consistent with structure. Unreacted 2-cyano-N-(cyclohexylmethyl)acetamide was also recovered (10.70 g, 51%).

2-Cyano-N-(cyclohexylmethyl)acetamide (from step (a) example 13, 7.66 g, 42.5 mmol) was also condensed with butyl isocyanate (Adrich, 7.60 ml, 63.7 mmol) in anhydrous toluene (70 mL) in a Parr bomb at 120° C. for 24 h to provide 1-butyl-3-(2-cyanoacetyl)-1-(cyclohexylmethyl)urea (3.51 g, 30%). $^1$H-NMR (DMSO-d$_6$) consistent with structure. Unreacted 2-cyano-N-(cyclohexylmethyl)acetamide was also recovered (5.97 g, 70%).

In the manner of step (c) of Example 13, 1-butyl-3-(2-cyanoacetyl)-1-(cyclohexylmethyl)urea from above (8.515 g, 30 mmol) was converted to 6-amino-1-butyl-3-(cyclohexylmethyl)uracil, isolated as a pale yellow crystalline solid (8.008 g, 94%). $^1$H-NMR (DMSO-d$_6$) consistent with structure. A portion of this material (7.598 g, 27 mmol) was then nitrosated in the manner of step (c) of Example 1 to afford 6-amino-1-butyl-3-(cyclohexylmethyl)-5-nitrosouracil as a pink solid (7.771 g, 93%), m.p. 229°–230° C. with dec.; $^1$H-NMR (DMSO-d$_6$) consistent with structure.

Anal. Calcd for C$_{15}$H$_{24}$N$_4$O$_3$: C, 58.42; H, 7.84; N, 18.17. Found: C, 58.33; H, 7.80; N, 18.21.

(b) (E)-4-[3-Butyl-1-(cyclohexylmethyl)-1,2,3,6-tetrahydro-2,6-dioxo-9H-purin-8-yl]cinnamic acid In the manner of step (d) of Example 1, 6-amino-1-butyl-3-(cyclohexylmethyl)-5-nitrosouracil (from step (a), 2.467 g, 8.0 mmol) was converted to (E)-4-[3-butyl-1-(cyclohexylmethyl)-1,2,3,6-tetrahydro-2,6-dioxo-9H-purin-8-yl]cinnamic acid, isolated as a pale yellow powder (2.2842 g, 62%), m.p. >350° C.; $^1$H-NMR (DMSO-d$_6$) consistent with structure.

Anal. Calcd for C$_{25}$H$_{30}$N$_4$O$_4$·0.40 H$_2$O: C, 65.60; H, 6.78; N, 12.24. Found: C, 65.60; H, 6.74; N, 12.29.

EXAMPLE 15

(E)-N-Benzyl-4-(1,3-bis(cyclohexylmethyl)-1,2,3,6-tetrahydro-2,6-dioxo-9H-purin-8yl)cinnamide N,N'-Carbonyldiimidazole (Lancaster Synthesis, 120 mg, 0.74 mmol) was added to a pale yellow slurry of (E)-4-[1,3-bis(cyclohexylmethyl)-1,2,3,6-tetrahydro-2,6-dioxo-9H-purin-8-yl]cinnamic acid (from step (d) example 1, 250 mg, 0.51 mmol) in anhydrous DMF (3 mL)-THF (3 mL) under nitrogen The slurry was briefly warmed to ca 45° C., and then stirred for 2 h, during which time it became bright yellow as a gas evolved. Benzylamine (Aldrich, 250 mg, 2.3 mmol) was then added, and the mixture was stirred for 4 d. Volatiles were then removed in vacuo, and the resulting residue was chromatographed on silica gel. The title comnpound eluted in 4% ethanol in chloroform to provide a white powder after trituration with acetonitrile (229 mg, 77%), m.p. 276°–279° C.; $^1$H-NMR (DMSO-d$_6$) consistent with structure.

Anal. Calcd for C$_{35}$H$_{41}$N$_5$O$_3$: C, 72.51; H, 7.13; N, 12.08. Found: C, 72.52; H, 7.18; N, 12.07.

EXAMPLE 16

(E)-Ethyl-4-[1,3-bis(cyclohexylmethyl)-1,2,3,6-tetrahydro-2,6-dioxo-9H-purin-8-yl]cinnamate N,N'-Carbonyldiimidazole (Lancaster Synthesis, 908 mg, 5.6 mmol) was added to a pale yellow slurry of (E)-4-[1,3 bis(cyclohexylmethyl)-1,2,3,6-tetrahydro-2,6-dioxo-9H-purin-8-yl]cinnamic acid (from step (d) example 1, 1.962 g, 4.0 mmol) in anhydrous DMF (15 mL)-THF (15 mL) under nitrogen. The slurry was stirred for 3.75 h, during which time it became bright yellow as a gas evolved. Absolute ethanol (460 mL, 8 mmol) was then added, followed by DBU (Aldrich, 837 mL, 5.6 mmol). Addition of the base produced a deep red reaction mixture and caused almost complete dissolution of the acyl imidazole. After stirring for 18 h, the reaction mixture was treated with an additional equivalent of absolute ethanol (230 mL, 4 mmol). The orange solution was stirred for 2.5 h before volatiles were removed at 1Torr. The resulting brown mixture was chromatographed on silica gel, eluting with a gradient from 0–6% methanol in dichloromethane. The title compound eluted in 0–1% methanol in dichloromethane as an off-white solid (1.643 g, 79%). Recrystallization from dichloromethane-hexanes provided a white powder (1.501 g, 72%), m.p. >300° C.; $^1$H-NMR (DMSO-d$_6$) consistent with structure.

Anal. Calcd for C$_{30}$H$_{38}$N$_4$O$_4$: C, 69.47; H, 7.38; N, 10.80. Found: C, 69.39; H, 7.37; N, 10.86.

A second ester eluted from the column above in 5% methanol in dichloromethane (422 mg). Recrystallization from ca 1% methanol in dichloromethane, followed by washing with hexanes provided ethyl 3-{4-|1,3-bis(cyclohexylmethyl)-1,2,3,6-tetrahydro-2,6-dioxo-9H-purin-8-yl]phenyl}-3-(1H-imidazol-1-yl)propionate as a light yellow powder (414 mg, 17%); m.p. 231°–232° C. (dec);

$^1$H-NMR (DMSO-d$_6$) d: 13.80 (br s, 1, NH), 8.06 (d, J=8.5 Hz, 2, 2 phenyl CH), 7.88 (m, 1, imidazole CH), 7.54 (d, J=8.3 Hz, 2, 2 phenyl CH), 7.38 (m, 1, imidazole CH), 6.88 (m, 1, imidazole CH), 5.84 (m, 1, benzyl CH), 3.99 (q, J=7.2 Hz, 2, CO$_2$CH$_2$), 3.88 (d, J=6.6 Hz, 2, CH$_2$N), 3.75 (d, J=7.7 Hz, 2, CH$_2$N), 3.42 (m, 2, CH$_2$CO$_2$),1.9-1.5 and 1.2-0.8 (both br m, 22 total, 2 cyclohexyl), 1.06 (t, J=7.1 Hz, 3, CH$_3$). Anal. Calcd for C$_{33}$H$_{42}$N$_6$O$_4$·0.30 H$_2$O: C, 67.98; H, 6.84; N, 15.71. Found: C, 67.93; H, 6.67; N, 15.92.

EXAMPLE 17

(E)-3-[(1,3-Bis(cyclohexylmethyl)-1,2,3,6-tetrahydro-2,6-dioxo-9H-purin-8-yl]cinnamic Acid In the manner of step (d) of Example 1, 6-amino 1,3-bis(cyclohexylmethyl)-5-nitrosouracil (from step (c) example 1, 2.79 g, 8.00 mmol) was reduced to 1,3-bis(cyclohexylmethyl)-5,6-diaminouracil, which was condensed with 3-formylcinnamic acid (T. Higa, A. J. Krubsack, J. Org. Chem. 1975, 40: 3037–3045, 1.424 g, 8.00 mmol) to give (E)-3-[1,3-bis(cyclohexylmethyl)-1,2,3,6-tetrahydro-2,6-dioxo-9H-purin-8-yl]cinnamic acid as an off-white solid (1.947 g, 49%), m.p. >350° C.; $^1$H-NMR (DMSO-d$_6$) consistent with structure.

Anal. Calcd for $C_{28}H_{34}N_4O_4 \cdot 0.10\ H_2O$: C, 68.30; H, 7.00; N, 11.38. Found: C, 68.33; H, 6.93; N, 11.34.

EXAMPLE 18

(E)-3-[3-(Cyclohexylmethyl)-1,2,3,6-tetrahydro-2,6-dioxo-1-propyl-9H-purin-8-yl]cinnamic Acid In the manner of step (d) of Example 1, 6amino-1-(cyclohexylmethyl)-3-propyl-5-nitrosouracil (step (c) example 12, 2.355 g, 8.00 mmol) was reduced to 1-(cyclohexylmethyl)-5,6-diamino-3-propyluracil, which was condensed with 3-formylcinnamic acid (T. Higa, A. J. Krubsack, J. Org. Chem. 1975, 40: 3037–3045, 1.424 g, 8.00 mmol) to give (E)-3-[3-(cyclohexylmethyl)-1,2,3,6-tetrahydro-2,6dioxo-1-propyl-9H-purin-8-yl]cinnamic acid as a pale yellow solid (2.632 g, 75%), m.p. >350° C.; $^1$H-NMR (DMSO-d$_6$) consistent with structure.

Anal. Calcd for $C_{24}H_{28}N_4O_4$: C, 66.04; H, 6.46; N, 12.84. Found: C, 65.95; H, 6.52; N, 12.77.

EXAMPLE 19

(E)-4-(1,3-Bis(cyclohexylmethyl)-1,2,3,6-tetrahydro-6-oxo-2-thioxo-9H-purin-8-yl]cinnamic Acid (a) 1,3-Bis(cyclohexylmethyl)thiourea A solution of N,N'-thiocarbonyldiimidazole (Aldrich, 90%, 3.64 g, 18.4 mmol) in chloroform (20 mL) was added dropwise to a solution of cyclohexanemethylamine (Aldrich, 98%, 5.00 g, 4.33 mmol) in chloroform (10 mL). The reaction mixture was then stirred at 50° C. for 2 h, cooled to ambient temperature, and washed with hydrochloric acid (0.1N, 3×50 mL) and water (50 mL). The organic layer was dried (magnesium sulfate), and concentrated under vacuum to a yellow solid, which was recrystallized from ethanol. The mother liquor from this crystallization was concentrated, and the resulting solid was recrystallized from toluene. The two crops of crystals were combined and dried under vacuum to provide 1,3-bis(cyclohexylmethyl)thiourea as a pale yellow powder (4.19 g, 85%), m.p. 124°–125° C.; $^1$H-NMR (DMSO-d$_6$) consistent with structure.

Anal. Calcd for $C_{15}H_{28}N_2S$: C, 67.11;H, 10.51; N, 10.44; S, 11.94 Found: C, 67.16; H, 10.51; N, 10.43; S, 11.89.

(b) 6-Amino-1,3-bis(cyclohexylmethyl)-1,2-dihydro-2-thioxo-4(3H)-pyrimidinone

A solution of cyanoacetic acid (Aldrich, 1.23 g, 14.3 mmol) and 1,3-bis(cyclohexylmethyl)thiourea (from step (a), 3.50 g, 13.0 mmol) in acetic anhydride (8.1 mL) was stirred at 70° C. for 2 h under nitrogen. Volatiles were removed in vacuo and the residual oil was dried by evaporation of portions of 10% water-ethanol (3×50 mL). The resulting solids were dissolved in ethanol (12 mL)-water (28 mL) at reflux with adjustment of the pH to 11 by addition of 10% aqueous sodium carbonate. After 1 h, the mixture was cooled to ambient temperature, volatiles were removed under vacuum, and the residue was chromatographed on silica gel. 6-Amino-1,3-bis(cyclohexylmethyl)-1,2-dihydro-2-thioxo-4(3H)-pyrimidinone eluted with 4% methanol in chloroform, and was recrystallized from 2% ethyl acetate in hexanes to provide an off-white powder (2.27 g, 50%), m.p. 147°–150° C.; $^1$H-NMR (DMSO-d$_6$) consistent with structure.

Anal. Calcd for $C_{18}H_{29}N_3SO.0.15\ C_6H_{12}$: C, 65.15; H, 9.00; N, 12.06: S, 9.20. Found: C,65.30; H, 8.86; N, 12.00; S, 9.27.

(c) 6-Amino-1,3-bis(cyclohexylmethyl)-1,2-dihydro-5-nitroso-2-thioxo-4(3H)-pyrimidinone In the manner of step (c) of Example 1, 6-amino-1,3-bis(cyclohexylmethyl)-1,2-dihydro-2-thioxo-4(3H)-pyrimidinone (from step (b), 30.9 g, 92.1 mmol) was converted to 6-amino-1,3-bis(cyclohexylmethyl)-1,2-dihydro-5-nitroso-2-thioxo-4(3H)-pyrimidinone, isolated as a green powder (20.17 g, 60%), m.p. 232°–235° Cl $^1$H-NMR (DMSO-d$_6$) consistent with structure.

Anal. Calcd for $C_{18}H_{28}N_4SO_2$: C, 59.31; H, 7.74; N, 15.37; S, 8.80. Found: C 59.41; H, 7.75; N, 15.31; S, 8.75.

(d) (E)-4-(1,3-Bis(cyclohexylmethyl)-1,2,3,6-tetrahydro-6-oxo-2-thioxo-9H-purin-8-yl)cinnamic acid In the manner of step (d) of example 8, 6-amino-1,3-bis(cyclohexylmethyl-1,2-dihydro-5-nitroso-2-thioxo-4(3H)-pyrimidinone (from step (c), 3.00 g, 8.20 mmol) was reduced to 1,3-bis(cyclohexylmethyl)-5,6-diamino-1,2-dihydro-2-thioxo-4(3H)-pyrimidinone, which was then combined with 4-formylcinnamic acid (Aldrich, 1.44 g, 8.20 mmol) in ethanol (150 mL). The resulting yellow mixture was dried by evaporation of several portions of absolute ethanol, and the residual yellow powder (Schiff base intermediate) was heated at reflux in nitrobenzene (150 mL) until no more water distilled off. The reaction mixture was then cooled to ambient temperature, and stirred in ether (200 mL). The resulting pale yellow precipitate was filtered off, washed with hot ethanol (100 mL), followed by ether (100 mL), and dried under vacuum at 110° C. to afford (E)-4-(1,3-bis(cyclohexylmethyl)-1,2,3,6-tetrahydro-6-oxo-2-thioxo-9H-purin-8-yl)cinnamic acid as a yellow powder (2.32 g, 65%), m.p. >300° C.; $^1$H-NMR (DMSO-d$_6$) consistent with structure.

Anal. Calcd for $C_{28}H_{34}N_4SO_3 \cdot 0.25\ H_2O$: C, 65.79; H, 6.80; N, 10.96; S, 6.27. Found: C 65.80; H, 6.81; N, 11.01; S, 6.18.

Pharmaceutical Formulation Examples

In the following Examples, the "active ingredient" may be any compound of formula (I) or a pharmaceutically acceptable salt, solvate, ester, or amide thereof (1) Tablet formulations

| (i) Oral | mg/tablet | | |
|---|---|---|---|
| | A | B | C |
| Active ingredient | 25 | 25 | 25 |
| Avicel | 13 | — | 7 |
| Lactose | 78 | 47 | — |
| Starch (maize) | — | 9 | — |
| Starch (pregelatinised, NF15) | — | — | 32 |
| Sodium starch glycollate | 5 | — | — |
| Povidone | 3 | 3 | — |
| Magnesium stearate | 1 | 1 | 1 |
| | 125 | 85 | 65 |

21
-continued

| (ii) Sublingual | mg/tablet | |
| --- | --- | --- |
| | D | E |
| Active ingredient | 25 | 25 |
| Avicel | 10 | — |
| Lactose | — | 36 |
| Mannitol | 51 | 57 |
| Sucrose | — | 3 |
| Acacia | — | 3 |
| Povidone | 3 | — |
| Magnesium stearate | 1 | 1 |
| | 90 | 125 |

Formulations A to E may be prepared by wet granulation of the first six ingredients with the povidone, followed by addition of the magnesium stearate and compression.

| (iii) Buccal | mg/tablet |
| --- | --- |
| Active ingredient | 25 |
| Hydroxypropylmethyl cellulose (HPMC) | 25 |
| Polycarbophil | 39 |
| Magnesium stearate | 1 |
| | 90 |

The formulation may be prepared by direction compression of the admixed ingredients.

(2) Capsule formulations

| (i) Powder | mg/Capsule | |
| --- | --- | --- |
| | F | G |
| Active ingredient | 25 | 25 |
| Avicel | 45 | — |
| Lactose | 153 | — |
| Starch (1500 NF) | — | 117 |
| Sodium starch glycollate | — | 6 |
| Magnesium stearate | 2 | 2 |
| | 225 | 150 |

Formulations F and G may be prepared by admixing the ingredients and filing two-part hard gelatin capsules with the resulting mixture.

| (ii) Liquid fill | mg/Capsule | |
| --- | --- | --- |
| | H | I |
| Active ingredient | 25 | 25 |
| Macrogol 4000 BP | 200 | — |
| Lecithin | — | 100 |
| Arachis oil | — | 100 |
| | 225 | 225 |

Formulation H may be prepared by melting the Macrogol 4000 BP, dispersing the active ingredient in the melt and filling two-part hard gelatin capsules therewith. Formulation I may be prepared by dispersing the active ingredient in the lecithin and arachis oil and filling soft, elastic gelatin capsules with the dispersion.

22

| (iii) Controlled release | mg/tablet |
| --- | --- |
| Active ingredient | 25 |
| Avicel | 123 |
| Lactose | 62 |
| Triethylcitrate | 3 |
| Ethyl cellulose | 12 |
| | 225 |

The formulation may be prepared by mixing and extruding the first four ingredients and spheronising and drying the extrudate. The dried pellets are coated with ethyl cellulose as a release controlling membrane and filled into two-part, hard gelatin capsules.

(3) Intravenous injection formulation

| (i) | % by weight |
| --- | --- |
| Active ingredient | 2% |
| Sodium hydroxide) | q.s to pH 7 |
| Water for Injections | to 100% |

The active ingredient is taken up in the citrate buffer and sufficient hydrochloric acid added to affect solution and adjust the pH to 7. The resulting solution is made up to volume and filtered through a micropore filter into sterile glass vials which are sealed and oversealed.

| (ii) Cyclodextrin formulation | |
| --- | --- |
| Active ingredient | 0.1–25 mg |
| Hydroxypropyl β-cyclodextrin | amount depending on formulation |
| Sodium hydroxide | amount depending on formulation |
| Hydrochloric acid to adjust pH | amount depending on formulation |
| Sterile water q.s. to | 1 mL |
| pH of solution | pH 5.0–9.0 |

The active ingredient is dissolved in a water miscible solvent in which the compound is soluble. Hydroxypropyl β-cyclodextrin is dissolved in water. Different molar ratios of the hydroxypropyl β-cyclodextrin from 1:1 to 50:1 (hydroxypropyl β-cyclodextrin:drug) are used. The solution of the active ingredient is then added to the cyclodextrin solution until a clear solution of the complex is obtained. The pH of the solution is adjusted to pH 5.0–9.0 using hydrochloric acid or sodium hydroxide.

For example a 10.0 mg solution at a 10:1 molar ratio hydroxypropyl β-cyclodextrin:drug requires

| Active ingredient | 10 mg (0.02 M) |
| --- | --- |
| Hydroxypropyl β-cyclodextrin: | 276 mg (0.2 M) |

Similarly a 10 mg solution at a 5:1 molar ratio hydroxypropyl β-cyclodextrin:drug requires

| Active ingredient | 10 mg (0.02 M) |
| --- | --- |
| Hydroxypropyl β-cyclodextrin | 138 mg (0.1 M) |

This complex may be isolated by any suitable technique for example lyophilisation, evaporation of the solvent, or spray drying. P Use/Advantage: High concentrations of the active ingredient in solution can be obtained using the cyclodextrin complex. The lyophilized and spray dried complexes can be reconstituted to known concentrations. The cyclodextrin acts merely as a solubilizing agent without altering the therapeutic behaviour of the drug in any way.

EXAMPLE G

Powder Capsules for Inhalation

| | |
|---|---|
| Active Ingredient (0.5–7.0 μm powder) | 1.0 mg |
| Lactose (30–90 μm powder) | 49.0 mg |

The powders were mixed until homogeneous and filled into suitably sized hard gelatin capsules (50 mg per capsule).

EXAMPLE H

Inhalation Aerosol

| | |
|---|---|
| Active Ingredient (0.5–7.0 μm powder) | 50.0 mg |
| Sorbitan Trioleate | 100.00 mg |
| Saccharin Sodium (0.5–7.0 μm powder) | 5.0 mg |
| Methanol | 2.0 mg |
| Trichlorofluoromethane | 4.2 g |
| Dichlorodifluoromethane | to 10.0 ml |

The sorbitan trioleate and methanol were dissolved in the trichloro-fluoromethane. The saccharin sodium and active ingredient were dispersed in the mixture which was then transferred to a suitable aerosol canister and the dichlorofluoromethane injected through the valve system. This composition provides 0.5 mg of active ingredient in each 100 μl dose.

Biological Activity

1) Enzyme inhibition

Compounds of the invention were assayed for inhibiting activity in arachidonate metabolism and PAF synthesis as follows.

A) Arachidonate Metabolism

Arachidonate cyclooxygenase, 5-lipoxygenase, and thromboxane synthetase were assayed as described in White et al, Prostaglandins, Leukotrienes and Medicine, 1985; 20: p 1–9. Pleural exudate cells were harvested from Harlan Sprague-Dawley male rats (150±20 g) 3 hr after intrapleural injection of 0.5 mg carrageenan. Cell counts were obtained from pooled exudates, which were then centrifuged at 200 g (10 min, 4° C.) and resuspended at 15 million cells/ml in 0.13M NaCl, 15 mM Tris-Cl, 5 mM glucose, pH 7.4. Portions of this cell suspension (3 million cells per assay) were preincubated with and without compound being tested for 5 min at 37° C. in 50 mM Tris-Cl, 1 mM $CaCl_2$, pH 7.4. Ionophore A23187 (3 μM) and [$^{14}$C]arachidonate (to give 10 μM; 55 Ci/mol) were then added in a total assay volume of 400 μl, and incubation was continued for 2 min at 37° C. Blank assays were performed using sonicated cells with 0.1 mM 3-amino-1-m-trifluoromethylphenyl pyrazol-2-ine, an inhibitor of cyclooxygenase and lipoxygenase pathways. After incubation, reaction mixtures were acidified with 20 μl of 2N HCl and extracted with 4 ml diethyl ether. Ether extracts were dried under nitrogen, resuspended in ethyl acetate, and chromatographed on Whatman LK5D silica gel G plates, using ethyl acetate/isooctane/acetic acid/water (9/5/2/10; vols; top layer after 5 min shaking). Thin layer plates were exposed to Kodak SB-5 X-ray film to produce autoradiogran. [$^{14}$C]DPM in products were obtained by scraping appropriate regions of TLC plates and counting in a scintillation spectrometer. Effects on the 5-lipoxygenase pathway were estimated by counting 5-HETE and 5,12-diHETE ($LTB_4$). Cyclooxygenase and thromboxane synthetase inhibition were estimated by counting thromboxane $B_2$ and prostaglandin $E_2$ or $F_2\alpha$. Selective thromboxane inhibitors will decrease thromboxane $B_2$ and increase $PGE_2$ and $PGF_2\alpha$. Cyclooxygenase inhibitors will inhibit the formation of all three products.

B) Lyso-PAF: Acetyl-CoA Acetyltransferase [Synthesis of Platelet-Activating Factor (PAF)]

Synthesis of PAF (platelet-activating factor) was measured in a lysate of rat pleural neutrophils, as described by White and Faison, Prostaglandins, 1988; 35: p939–44. Pleural exudate cells, harvested from male Harlan Sprague-Dawley rats (150±20 g) 3 hr after injection of 0.5 mg carrageenan, were centrifuged at 200 g for 10 min at 4° C., washed, and resuspended at approximately 17 million cells/ml in a buffer consisting of 50 mM potassium phosphate, 144 mM NaCl, 6 mM KCl, 5 mM glucose, 1 mM $MgCl_2$, 1.3 mM $CaCl_2$, pH 7.4. Resuspended cells were incubated with calcium ionophore A23187 (1 μM) for 5 min at 37° C. to activate the acetyltransferase and then centrifuged at 755 g for 2 min at 4° C. Pellets were resuspended in cold distilled water and sonicated in a 50 Hz ultrasonic bath. Portions (250 μl) of the resulting lysate were mixed with buffer, test compound, and substrates to give 36 mM Tris-Cl, pH 6.9, 12 μM lyso-PAF, and 2.3 μM [$^{14}$C]acetyl-CoA (0.06 μCi) in a total volume of 500 μl. Blank assays contained nonactivated neutrophils and no added lyso-PAF. The compound being tested was added prior to substrates. After incubation at 37° C. for 10 min, 0.68 ml of 2N HCl and 2.53 ml of 1:1 chloroform/methanol were added to each tube to extract labeled PAF. Each tightly-covered tube was briefly sonicated in a Branson 50 Hz bath, vortexed for 20 sec, and centrifuged at 160 g for 5 min to separate solvent phases. A 0.90 ml aliquot of the lower (organic)phase was pipetted into a glass scintillation vial, dried under nitrogen using an N-EVAP apparatus (Organomation Associates), and counted using scintillation techniques.

2) Compounds of the invention were assayed for inhibition of Antigen-Induced airway eosinophilia as follows:

Male Hartley guinea pigs [Crl:(HA)Br, Charles River] weighing 200–300 g were sensitized to ovalbumin (OA) by intraperitioneal (i.p.) injections (in 1 ml 0.9% saline) of 20 mg followed by 1 mg 2 or 3 days later. After four to twelve weeks, the animals were treated with the antihistamine, pyrilamine (1 mg/kg i.p), 1 hour prior to exposure (17.8 l chamber) and for 10 min to an aerosol of OA (0.5% w/v solution in 0.9% sterile saline) generated from a jet nebulizer (Devilbiss Model 40; flow rate=8.5 l/min). Test compounds were suspended in 0.5% w/v methycellulose in water and administered i.p. (dose volume=1 ml/kg) at 10 mg/kg, 1 h before and 7 h following aerosolized antigen. Twenty-four hours after antigen challenge, each animal was anesthetized with sodium pentobarbital (55–75 mg/kg i.p.), the trachea cannulated and the lungs lavaged with 4×10 ml aliquots of Hanks' Balanced Salt Solution warmed to 37° C. The aliquots were pooled in 40 ml polycarbonate centrifuge tubes, centrifuged (200 g for 10 min at 4° C.) and the cell pellet resuspended in HEPES buffered solution (2 ml). Fifty μl of the suspension were added to 10 ml of Isoton Diluent (Fisher Scientific) containing three drops of lysing agent and the cells counted with a Coulter Counter (Model ZB1). Four μl of the cell suspension were spread on a 3×1 inch glass microscope slide, allowed to dry and the cells stained with DIFF-QUIK™ (Fisher Scientific). Two slides were prepared for each animal. Differential cell counts were made (100× magnification) from a minimum of four fields on 100 cells per slide (total cells counted per animal=200), using standard morphological criteria to classic cells into eosinophils, neutrophils, lymphocytes and macrophages. The activity of the test compound was calculated by comparing the mean proportions of eosinophils in the lavage fluid of compound-treated animals with controls (vehicle-treated animals) and expressing as percent inhibition.

Results

TABLE 1

Results of enzyme inhibition assays and assays of inhibition of antigen-induced airway eosinophilia in the guinea pig

| Example | Enzymes $IC_{50}(\mu M)$ | | | Inhibition of Airway Eosinophilia | |
|---|---|---|---|---|---|
| | PAF | 5-LO | CO | Dose (ip) (mg/kg) | (% inhibition) |
| 1 | 2.5 | 0.3 | 0.1 | 5 | 50% |
| 4 | 15 | 6 | 5 | 10 | 46% |
| 7 | 12 | 1.5 | 4 | 6.8 | 50% |

3) In vivo Septic Shock model C. parvum/LPS Shock

Male CD-1 mice, 25–30 g (Charles River: Raleigh, N.C.), are injected intravenously (i.v.) with 100 µg killed C. parvum (Coparvax; Burroughs Wellcome, RTP, NC). Nine or ten days later the mice are injected i.v. with 20 µg E. coli 026:B6 lipopolysaccharide (LPS; Difco Labs, Detroit, Mich.) in the presence of the analgesic butorphanol (150 µg per mouse). (E)-4-(1,3-bis(cyclohexylmethyl)-1, 2, 3, 6-tetrahydro-2, 6dioxo-9H-purin-8-yl)cinnamic acid was dissolved in ENCAPSIN (hydroxypropyl-β-cyclodextrin) for i.v. dosing before, at the same time as, and after the endotoxin. Control (untreated) animals go into shock within the first 90 min following LPS administration, and approximately 50% die within 3–5 hr. Mice are monitored for the first 7 hr and at 24 and 48 hr for survival.

Results (E)-4-(1,3-bis(cyclohexylmethyl)-1, 2, 3, 6-tetrahydro-2, 6-dioxo-9H-purin-8-yl) cinnamic acid was administered at 0.001 to 80 mg/kg i.v. in the Septic Shock model described above. The results are given in Table 2.

The compound was highly effective in decreasing mortality (greater than 50% protection being seen) when administered 2 hr before and at the time of LPS administration.

TABLE 2

(E)-4-(1,3-bis(cyclohexylmethyl)-1,2,3,6-tetrahydro-2, 6-dioxo-9H-purin-8-yl) cinnamic acid treatment of C.Parvum/ LPS Septic Shock in Mice: Dosed minus Two Hr and at time of LPS

| Dose of Compound[a] (mg/kg) | Schedule[b] (hr) | Alive/Total at: | | % Survival After 48 hr |
|---|---|---|---|---|
| | | 3 hr | 48 hr | |
| 0.001 | −2,0 | 6/8 | 1/8 | 13 |
| 0.01 | −2,0 | 7/8 | 1/8 | 13 |
| 0.1 | −2,0 | 6/8 | 4/8 | 50 |
| 1.0 | −2,0 | 6/8 | 7/8 | 88 |
| 5.0 | −2,0 | 7/8 | 6/8 | 75 |
| 10 | −2,0 | 8/8 | 6/8 | 75 |
| 20 | −2,0 | 8/8 | 6/8 | 75 |
| 40 | −2,0 | 7/8 | 6/8 | 75 |
| 60 | −2,0 | 7/8 | 6/8 | 75 |

TABLE 2-continued (E)-4-(1,3-bis(cyclohexylmethyl)-1,2,3,6-tetrahydro-2, 6-dioxo-9H-purin-8-yl) cinnamic acid treatment of C.Parvum/ LPS Septic Shock in Mice: Dosed minus Two Hr and at time of LPS

| Dose of Compound[a] (mg/kg) | Schedule[b] (hr) | Alive/Total at: | | % Survival After 48 hr |
|---|---|---|---|---|
| | | 3 hr | 48 hr | |
| 80 | −2,0 | 7/8 | 5/8 | 63 |
| — | −2,0 | 5/8 | 1/8 | 13 |

[a]Compounds dosed i.v. solubilized with ENCAPSIN (hydroxypropyl-β-cyclodextrin); control animals received ENCAPSIN without compound.
[b]C. parvum: 100 µg/mouse dosed i.v. LPS: 20 µg/mouse dosed i.v. 10 days after C. parvum Compound dosed i.v. 2 hr before LPS and at the time of LPS

We claim:
1. A compound of the formula (I):

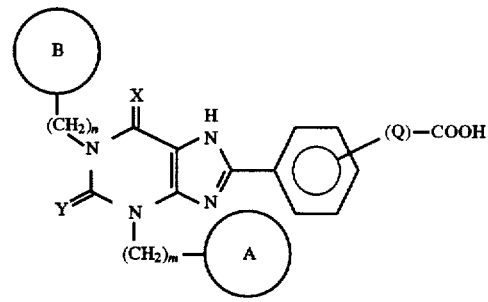

Wherein m and n are independently integers from 0 to 10;

X and Y are independently oxygen or sulphur;

(—Q—) is (—$CH_2$—)$_p$ or (—CH=CH—)$_p$ where p is an integer of from 1 to 4; and A and B are independently methyl, branched $C_{3-6}$ alkyl $C_{3-8}$ cycloalkyl or $C_{3-8}$ cycloalkenyl;

with the proviso that at least one of A and B is either $C_{3-8}$ cycloalkyl or $C_{3-8}$ cycloalkenyl;

or a salt, solvate, or pharmaceutically acceptable ethyl ester, methyl ester, or benzyl amide thereof.

2. A compound as claimed in claim 1 wherein;

m and n are both 1;

(Q) is attached at the 4 position and is —CH=CH—; and

X and Y are both oxygen or a salt, solvate, or pharmaceutically acceptable ethyl ester, methyl ester, or benzyl amide thereof.

3. (E)-4-(1,3-Bis(cyclohexylmethyl1, 2, 3, 6-tetrahydro-2, 6-dioxo-9H-purin-8-yl)cinnamic acid or a salt, solvate, or pharmaceutically acceptable ethyl ester, methyl ester, or benzyl amide thereof.

4. A method for the prophylaxis or treatment of clinical condition in a mammal or a human, requiring the inhibition of one or more of arachidonate 5-lipoxygenase, arachidonate cyclooxygenase, and lyso-PAF:acetyl-CoA acetyltransferase; which comprises administration of a therapeutically effective amount of compound of formula (I) according to claim 1, or a pharmaceutically acceptable salt, solvate, ethyl ester, methyl ester, or benzyl amide thereof.

5. Pharmaceutical compositions comprising a compound of formula (I) according to claim 1, or a pharmaceutically acceptable salt, solvate, ethyl ester, methyl ester, or benzyl amide together with at least one pharmaceutical carrier or recipient.

6. A process for preparing the compounds of formula (I) according to claim 1, or salts, solvates, or pharmaceutically acceptable ethyl ester, methyl ester, or benzyl amide thereof which comprises cyclising a compound of formula (II)

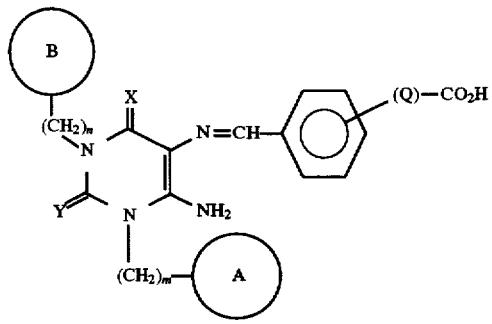
(II)

wherein A, B, m, n, X, Y, and Q are as defined for the compound of formula (I);

and optionally converting the compound of formula (I), (E)-4-1,3 Bis(cyclohexylmethyl)-1,2,3,6-tetrahydro-2,6-dioxo-9H-purin-8-yl cinnamic acid, to a different compound of formula (I), 3-{4-1,3 Bis(cyclohexylmethyl)-1,2,3,6-tetrahydro-2,6-dioxo-9H-purin-8-yl phenyl} propionic acid or a corresponding salt, solvate, or pharmaceutically acceptable ethyl ester, methyl ester, or benzyl amide.

* * * * *